US010221221B2

(12) United States Patent
Shaner et al.

(10) Patent No.: US 10,221,221 B2
(45) Date of Patent: Mar. 5, 2019

(54) MONOMERIC YELLOW-GREEN FLUORESCENT PROTEIN FROM CEPHALOCHORDATE

(71) Applicant: Allele Biotechnology & Pharmaceuticals, Inc., San Diego, CA (US)

(72) Inventors: Nathan C. Shaner, San Diego, CA (US); Gerard G. Lambert, San Diego, CA (US); Yuhui Ni, San Diego, CA (US); Jiwu Wang, La Jolla, CA (US)

(73) Assignee: ALLELE BIOTECHNOLOGY & PHARMACEUTICALS, INC, San Diego, CA (US)

( * ) Notice: Subject to any disclaimer, the term of this patent is extended or adjusted under 35 U.S.C. 154(b) by 137 days.

(21) Appl. No.: 13/950,239

(22) Filed: Jul. 24, 2013

(65) Prior Publication Data
US 2014/0038267 A1  Feb. 6, 2014

Related U.S. Application Data

(60) Provisional application No. 61/675,237, filed on Jul. 24, 2012.

(51) Int. Cl.
| | | |
|---|---|---|
| *A61K 38/00* | (2006.01) | |
| *C07K 14/46* | (2006.01) | |
| *G06F 19/12* | (2011.01) | |
| *G06F 19/16* | (2011.01) | |
| *C07K 14/435* | (2006.01) | |

(52) U.S. Cl.
CPC ........ *C07K 14/46* (2013.01); *C07K 14/43504* (2013.01); *G06F 19/12* (2013.01); *G06F 19/16* (2013.01)

(58) Field of Classification Search
None
See application file for complete search history.

(56) References Cited

U.S. PATENT DOCUMENTS

| | | | |
|---|---|---|---|
| 6,800,733 B2 | 10/2004 | Tsien et al. | |
| 7,166,444 B2 | 1/2007 | Lukyanov et al. | |
| 2009/0286314 A1 | 11/2009 | Israelsson | |
| 2012/0093737 A1 | 4/2012 | Wang | |

OTHER PUBLICATIONS

Campbell et al., "A monomeric red fluorescent protein," *Proc. Natl. Acad. Sci. USA*, Jun. 11, 2002, 99(12):7877-7882.
Chalfie et al., eds., *Green Fluorescent Protein: Properties Applications, and Protocols*, 2nd edition, 2006, Wiley-Interscience, Hoboken, NJ.
Colyer et al., "A novel fluorescence lifetime imaging system that optimizes photon efficiency," *Microsc. Res. Tech.*, 2008, 71:201-213.
Goedhart et al., "Structure-guided evolution of cyan fluorescent proteins towards a quantum yield of 93%," *Nat. Comms.*, 2012, 3:751, 9 pages.
Gross et al., "The structure of the chromophore within DsRed, a red fluorescent protein from coral," *Proc. Natl. Acad. Sci. USA*, Oct. 24, 2000, 97(22):11990-11995.
Karasawa et al., "A green-emitting fluorescent protein from *Galaxeidae* coral and its monomeric version for use in fluorescent labeling," *J. Biol. Chem.*, Sep. 5, 2003, 278(36):34167-34171.
Karasawa et al., Cyan-emitting and orange-emitting fluorescent proteins as a donor/acceptor pair for fluorescence resonance energy transfer, *Biochem. J.*, 2004, 381:307-312.
Li et al., "Evolutionary and functional diversity of green fluorescent proteins in cephalochordates," *Gene*, 2009, 446:41-49.
Lyskov et al., "The RosettaDock server for local protein-protein docking," *Nucleic Acids Res.*, 2008, 36:W233-W238.
Magde et al., "Fluorescence quantum yields and their relation to lifetimes of rhodamine 6G and fluorescein in nine solvents: improved absolute standards for quantum yields," *Photochemistry and Photobiology*, 2002, 75(4):327-334.
Malo et al., "Crystal structure and Raman studies of dsFP483, a cyan fluorescent protein from *Discosoma striata*," *J Mol. Biol.*, 2008, 378:871-886.
Markwardt et al., "An Improved Cerulean Fluorescent Protein with Enhanced Brightness and Reduced Reversible Photoswitching," *PLoS ONE*, Mar. 2011, 6(3):e17896, 11 pages.
Merzlyak et al., "Bright monomeric red fluorescent protein with an extended fluorescence lifetime," *Nature Methods*, Jul. 2007, 4(7):555-557.
Miyawaki, "Development of probes for cellular functions using fluorescent proteins and fluorescent resonance energy transfer," *Annu. Rev. Biochem.*, 2011, 80:357-373.
Redford et al., "Polar plot representation for frequency-domain analysis of fluorescence lifetimes," *J. Fluoresc.*, Sep. 2005, 15(5):805-815.
Roy et al., "I-TASSER: a unified platform for automated protein structure and function prediction," *Nature Protocols*, Apr. 2010, 5(4):725-738.

(Continued)

*Primary Examiner* — Hope Robinson
(74) *Attorney, Agent, or Firm* — Duiane Morris LLP

(57) ABSTRACT

The present disclosure provides isolated nucleic acid sequences encoding a monomeric green/yellow fluorescent proteins, and fragments and derivatives thereof. Also provided is a method for engineering the nucleic acid sequence, a vector comprising the nucleic acid sequence, a host cell comprising the vector, and use of the vector in a method for expressing the nucleic acid sequence. The present invention further provides an isolated nucleic acid, or mimetic or complement thereof, that hybridizes under stringent conditions to the nucleic acid sequence. Additionally, the present invention provides a monomeric green/yellow fluorescent protein encoded by the nucleic acid sequence, as well as derivatives, fragments, and homologues thereof. Also provided is an antibody that specifically binds to the green/yellow fluorescent protein.

5 Claims, 8 Drawing Sheets
Specification includes a Sequence Listing.

(56) References Cited

OTHER PUBLICATIONS

Shaner et al., "Advances in fluorescent protein technology," *J. Cell. Sci.,* 2007, 120(24):4247-4260.

Shaner et al., "A guide to choosing fluorescent proteins," *Nature Methods,* Dec. 2005, 2(12):905-909.

Shaner et al., "Improved monomeric red, orange and yellow fluorescent proteins derived from *Discosoma* sp. Red fluorescent protein," *Nat. Biotechnol.,* Nov. 21, 2004, 22:1567-1572.

Shaner et al., "Improving the photostability of bright monomeric orange and red fluorescent proteins," *Nature Methods,* 2008, 5:545-551.

Subach et al., "An Enhanced Monomeric Blue Fluorescent Protein with the High Chemical Stability of the Chromophore," *PLoS ONE,* Dec. 2011, 6:e28674, 9 pages.

Sun et al., "Investigating protein-protein interactions in living cells using fluorescence lifetime imaging microscopy," *Nature Protocols,* 2011, 6(9):1324-1340.

Tsien, "The green fluorescent protein," *Annu. Rev. Biochem.,* 1998, 67:509-544.

Yarbrough et al., "Refined crystal structure of DsRed, a red fluorescent protein from coral, at 2.0-Å resolution," *Proc. Natl. Acad. Sci. USA,* Jan. 16, 2001, 98(2):462-467.

International Search Report and Written Opinion dated Feb. 10, 2014 in corresponding International Patent Application No. PCT/US13/51911, 11 pages.

Figure 4

```
                         10         20         30         40         50
LanYFP       ------------MSLPATHELHIFGSFNGVDFDMVGRGTGNPNDGYEELNLKSTKGALQFSP
dLanYFP      MVSKGEEDNMASLPATHELHIFGSFNGVDFDMVGRGTGNPNDGYEELNLKSTKGDLQFSP
mNeonGreen   MVSKGEEDNMASLPATHELHIFGSINGVDFDMVGQGTGNPNDGYEELNLKSTKGDLQFSP
                         ***********.********.******************* *****

60         70         80         90        100        110
LanYFP       WILVPQIGYGFHQYLPFPDGMSPFQAAMKDGSGYQVHRTMQFEDGASLTSNYRYTYEGSH
dLanYFP      WILVPQIGYGFHQYLPFPDGMSPFQAAMKDGSGYQVHRTMQFEDGASLTSNYRYTYEGSH
mNeonGreen   WILVPHIGYGFHQYLPYPDGMSPFQAAMVDGSGYQVHRTMQFEDGASLTVNYRYTYEGSH
             *****.**********.***********  **********************  ********

120        130        140        150        160        170
LanYFP       IKGEFQVIGTGFPADGPVMTNSLTAADWCVTKMLYPNDKTIISTFDWTYTTGSGKRYQST
dLanYFP      IKGEFQVIGTGFPADGPVMTNSLTAADWCVTKMLYPNDKTIISTFDWTYTTGNGKRYQST
mNeonGreen   IKGEAQVIGTGFPADGPVMTNSLTAADWCRSKKTYPNDKTIISTFKWSYTTGNGKRYRST
             ****.** ********************* .*  **********.*.****.****.**

180        190        200        210
LanYFP       VRTNYTFAKPMAANILKNQPMFVFRKTELKHSKTELNFKEWQKAFTDVM---------
dLanYFP      ARTNYTFAKPMAANILKNQPMFVFRKTELKHSKTELNFKEWQKAFTDVMDELYK
mNeonGreen   ARTNYTFAKPMAANYLKNQPMYVFRKTELKHSKTELNFKEWQKAFTDVMDELYK
             .**.**********.******.******************************
```

MONOMERIC YELLOW-GREEN FLUORESCENT PROTEIN FROM CEPHALOCHORDATE

RELATED APPLICATIONS

This application claims the benefit of the priority of U.S. provisional application Ser. No. 61/675,237, filed Jul. 24, 2012.

SEQUENCE LISTING

The instant application contains a Sequence Listing which has been submitted in ASCII format via EFS-Web and is hereby incorporated by reference in its entirety. Said ASCII copy, created on Oct. 7, 2013, is named F6035-00015_SL.txt, and is 8 kilobytes in size.

FIELD OF THE INVENTION

The present disclosure relates to novel monomeric yellow-green fluorescent proteins, termed mNeonGreen, which are derived/generated from a tetrameric fluorescent protein from the cephalochordate *Branchiostoma lanceolatum*. These exemplary monomeric versions of the proteins disclosed herein were designed and generated by structure and docking algorithms using protein engineering techniques and have no known close structural or functional homologs. The exemplary mNeonGreen monomeric fluorescent proteins described herein are among the brightest known in its class and have exceptional utility as a biomarker and/or protein fusion tag, and have shown great usefulness as a FRET acceptor for the newest generation of cyan fluorescent proteins.

BACKGROUND

Since the initial cloning of *Aequorea victoria* green fluorescent protein (avGFP) over 20 years ago, fluorescent proteins have become staples of biological imaging. After an initial flurry of activity leading to the development of avGFP variants in the blue to yellow-green wavelength range [1], the bulk of subsequent fluorescent protein research has focused on expanding the fluorescent protein color palette into the red region and improving the brightness and performance of these longer-wavelength variants [2], along with more recent improvements to cyan variants of avGFP (CFPs) [3,4]. Since green and yellow variants of the original avGFP (GFPs and YFPs) perform reliably for many applications, not much effort has been placed on developing novel fluorescent proteins in the green region of the spectrum. However, there is still room for improvement of green and yellow fluorescent proteins, both for routine imaging as well as more advanced applications such as Förster resonance energy transfer (FRET) [5].

SUMMARY OF THE INVENTION

In view of the above, the present disclosure provides novel green/yellow fluorescent proteins derived by protein engineering based on exemplary yellow fluorescent proteins from *Branchiostoma lanceolatum* (LanYFP, Allele Biotechnology, San Diego, Calif.), which exhibits an unusually high quantum yield (~0.95) and extinction coefficient (~150,000 M-1 cm-1). In certain embodiments, size exclusion chromatography revealed that these proteins are tetramers (FIG. 1).

In one aspect, the disclosure provides an exemplary compositions comprising a monomeric NeonGreen (mNeonGreen) protein having the sequence of SEQ ID NO: 1. In one embodiment, the composition comprises a protein having a polypeptide with at least 95% homology to the sequence set forth in SEQ ID NO:1. In one embodiment, the composition comprises a protein having a polypeptide with at least 97% homology to SEQ ID NO:1.

In one aspect, the present disclosure provides methods for monomerization of tetrameric LanYFP and compositions comprising thereof. In certain embodiments, the methods comprise the use of structure prediction algorithms coupled with modeling of the tetramer interfaces to guide the monomerization of LanYFP. In one embodiment, the structure prediction algorithm is based on well-conserved beta-barrel structures in fluorescent proteins.

In one aspect, the present disclosure provides an isolated nucleic acid sequence encoding a non-oligomerizing green/yellow Fluorescent Protein (having specific characteristic emission spectrum described below). In certain embodiments, the nucleic acid sequence may be compatible with mammalian (e.g., human) or other species' codon usage.

In another embodiment, the disclosure provides a nucleic acid sequence encoding a polypeptide that has at least about 95% homology with the polypeptide encoded by the nucleic acid of SEQ ID NO: 2. In yet another embodiment, a nucleic acid present in other than its natural environment, wherein said nucleic acid encodes a green/yellow chromoprotein or fluorescent mutant thereof, and wherein said nucleic acid has a sequence identity of at least about 90% with SEQ ID NO: 2.

In still another aspect, the present disclosure provides a vector that includes a nucleic acid sequence encoding a non-oligomerizing green/yellow Fluorescent Protein (FP). In one embodiment, the vector is a plasmid, a viral vector, or a linear form of DNA template. In another embodiment, the nucleic acid sequence of the vector is cDNA. Also provided is a host cell comprising the vector. The present invention further provides use of the vector in a method for expressing the nucleic acid sequence in mammalian cells, plant cells, yeast cells, bacterial cells, etc. In one embodiment, the nucleic acid sequence is expressed as a tandem genetic fusion to another protein.

In one embodiment, the novel protein may be a monomer or dimer. In a further embodiment, the lanYFP-derived fluorescent protein comprises at least one or more of the following mutations F15I, R25Q, A45D, Q56H, F67Y, K79V, S100V, F115A, I118K, V140R, T141S, M143K, L144T, D156K, T158S, S163N, Q168R, V171A, N174T, I185Y, F192Y.

In yet another aspect, the present disclosure provides an antibody that specifically binds to the FPs of the invention. In one embodiment, the antibody is a polyclonal antibody; in another embodiment, the antibody is a monoclonal antibody; in yet another embodiment, the antibody is a VHH protein.

Additional variations, aspects and advantages of the present invention will be apparent in view of the following descriptions. It should be understood, however, that the detailed description and the specific examples, while indicating preferred embodiments of the invention, are given for the purpose of illustration only, since various changes and modifications within the spirit and scope of the invention will become apparent to those skilled in the art from these detailed depictions and descriptions.

The exemplary proteins were detected with 480 nm excitation and 530 nm emission, compared to mCherry (monomer) detected with 540 nm excitation and 620 nm emission. Each exemplary fluorescent protein was run simultaneously with mCherry as a size standard with detection at both wavelengths; mCherry consistently eluted with the same peak shape and retention time. Curves are normalized to peak fluorescence.

Figure 1:
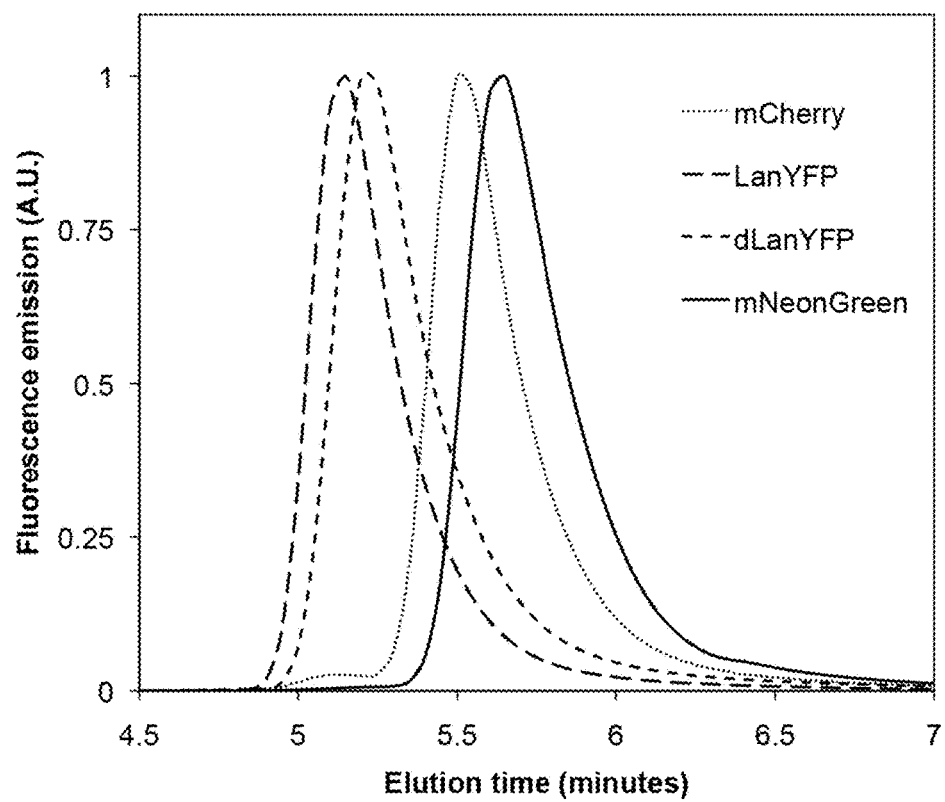
FIG. 1. Size exclusion chromatography of LanYFP (tetramer), dLanYFP (dimer), and mNeonGreen (monomer).
Figure 2:
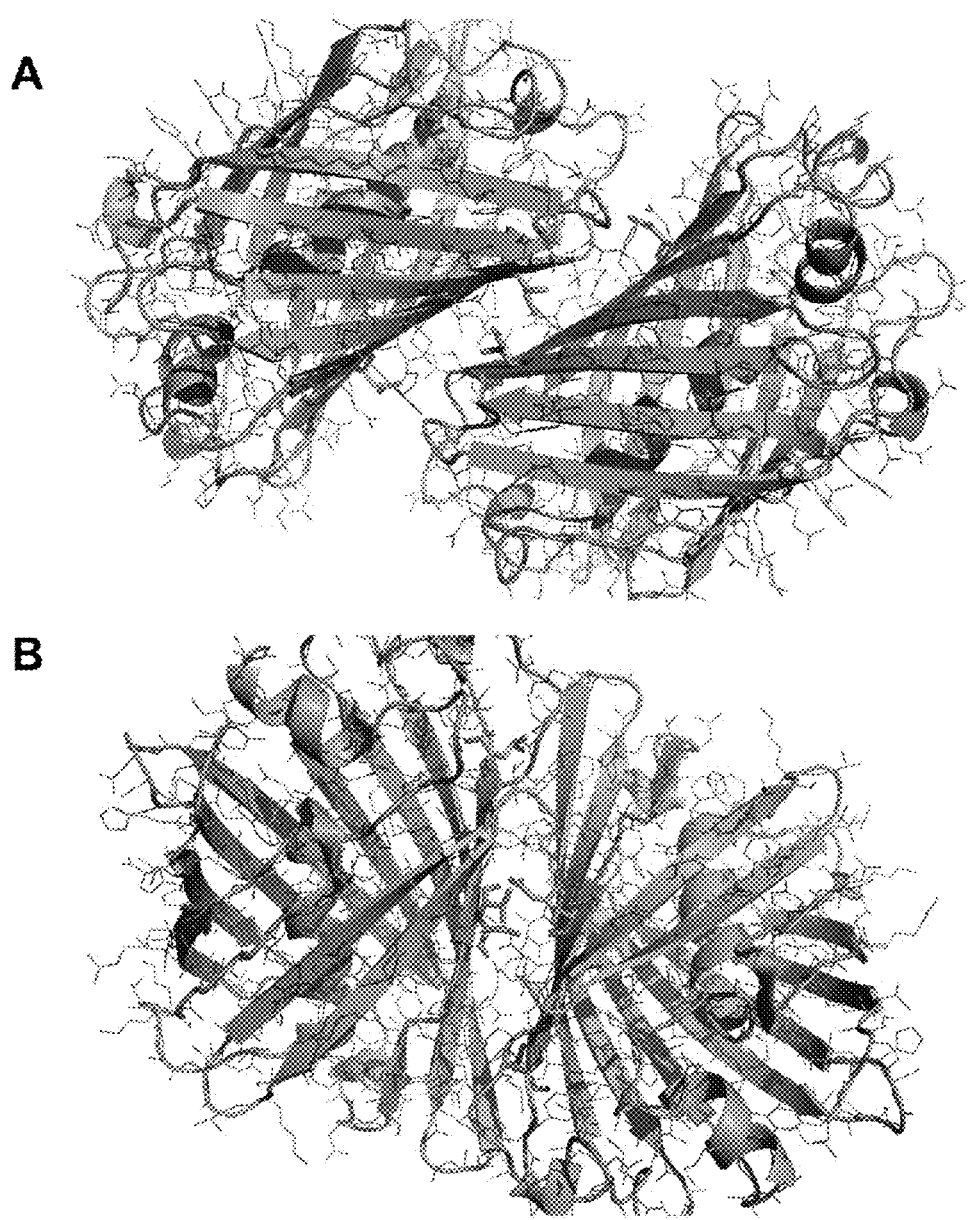

FIG. 2. Diagram of I-TASSER and RosettaDock models of wild-type LanYFP. (A) A/B dimer interface with targeted residues Ile118 and Asn174 shown as sticks and (B) A/C dimer interface with targeted residues Val140, Leu144, and Asp156 shown as sticks.

Figure 3:
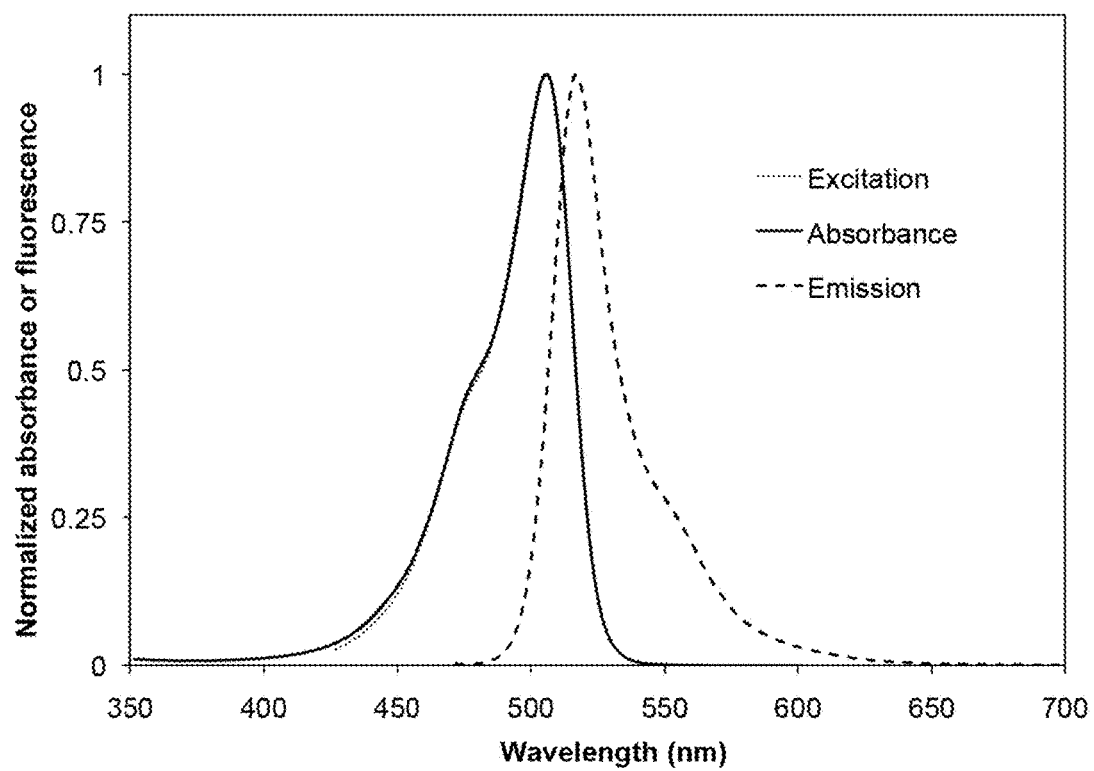

FIG. 3. Exemplary normalized absorbance, excitation, and emission spectra of mNeonGreen.

FIG. 4. Sequence alignment of LANYFP, dLANYFP, and mNeonGreen. AB interface mutations are shown in red, A/C interface mutations in yellow, and modified termini in green.

Figure 5:
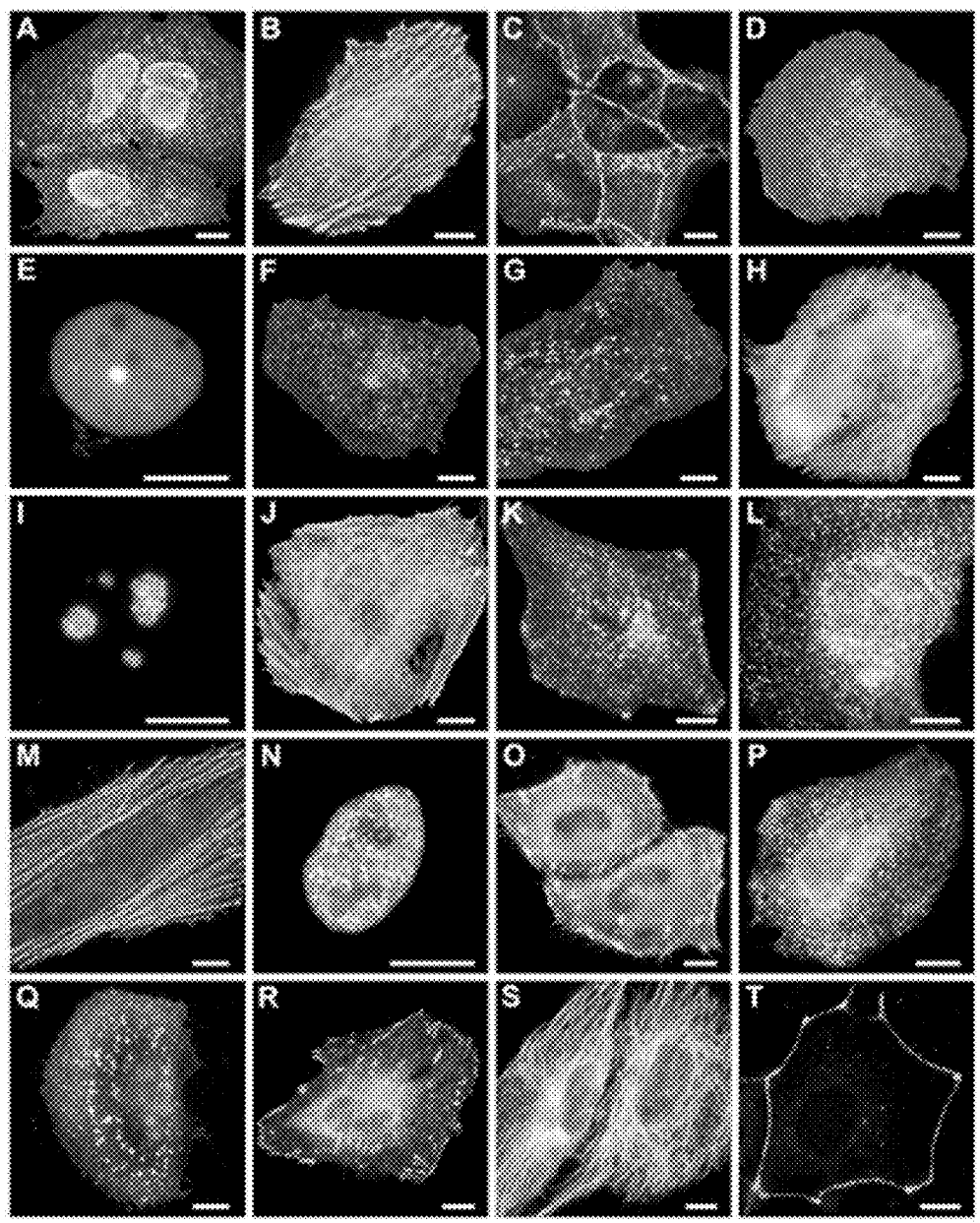

FIG. 5. Fluorescence imaging of mNeonGreen fusion vectors. Exemplary C-terminal mNeonGreen fusion constructs (with respect to the fluorescent protein); for each fusion, the linker amino acid length is indicated after the name of the targeted organelle or fusion partner: (A) mNeonGreen-Annexin (A4)-C-12 (human; plasma membrane); (B) mNeonGreen-β-actin-C-18 (human; actin cytoskeleton); (C) mNeonGreen-β-Catenin-C-20 (mouse; tight junctions); (D) mNeonGreen-CAAX-C-5 (20-amino acid farnesylation signal from c-Ha-Ras; plasma membrane); (E) mNeonGreen-CAF1-C-10 (mouse chromatin assembly factor); (F) mNeonGreen-Caveolin1-C-10 (human); (G) mNeonGreen-Endosomes-C-14 (human RhoB GTPase); (H) mNeonGreen-Fascin-C-10 (human; actin bundling); (I) mNeonGreen-Fibrillarin-C-7 (human; nucleoli); (J) mNeonGreen-FilaminA-C-14 (human; cytoskeleton); (K) mNeonGreen-LAMP1-C-20 (rat; lysosomal membrane glycoprotein 1; lysosomes); (L) mNeonGreen-Clathrin-C-15 (human, light chain B); (M) mNeonGreen-Myotilin-C-14 (human; actin filaments); (N) mNeonGreen-PCNA-C-19 (human; replication foci); (O) mNeonGreen-Plastin-C-10 (human; actin binding); (P) mNeonGreen-Rab4a-C-7 (human; endosomes); (Q) mNeonGreen-LC3B-C-7 (rat light chain; autophagosomes); (R) mNeonGreen-Talin-C-18 (mouse; focal adhesions); (S) mNeonGreen-Tubulin-C-35 (human; microtubules); (T) mNeonGreen-ZO1-C-14 (human; tight junctions). The cell line used for expression of C-terminal mNeonGreen constructs was Madin-Darby canine kidney (MDCK; ATCC, CCL-34) cells in panels C and T. HeLa CCL2 (ATCC) cells were used in the remaining panels. Scale bars represent 10 µm.

Figure 6:
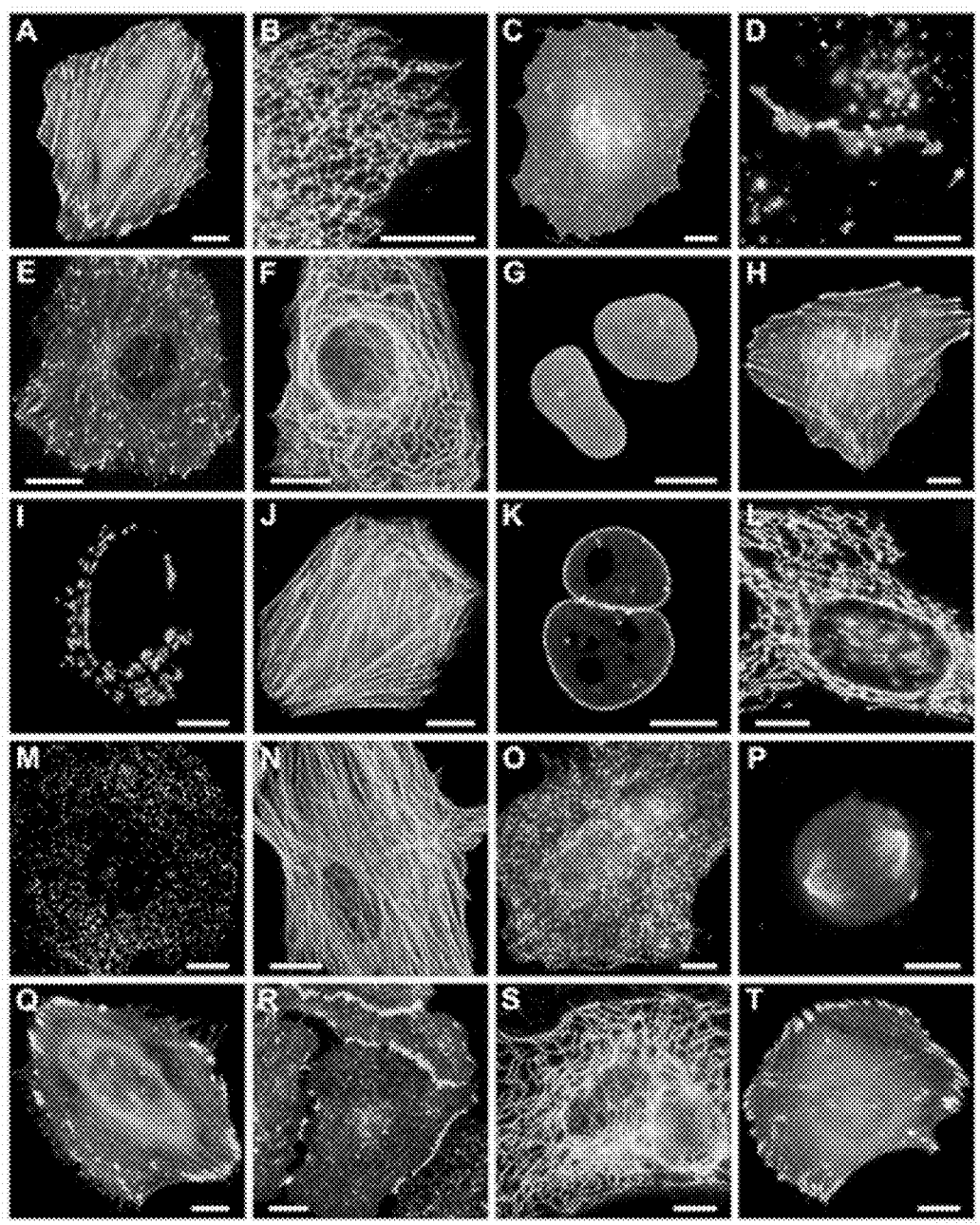

FIG. 6. Additional fluorescence imaging of mNeonGreen fusion vectors. Exemplary N-terminal mNeonGreen fusion constructs (with respect to the fluorescent protein); for each fusion, the linker amino acid length is indicated after the name of the targeted organelle or fusion partner: (A) mNeonGreen-α-Actinin-N-19 (human; non-muscle; actin and focal adhesions); (B) mNeonGreen-Calnexin-N-14 (human; endoplasmic reticulum); (C) mNeonGreen-C-Src-N-7 (chicken; plasma membrane); (D) mNeonGreen-Cx43-N-7 (rat α-1 connexin 43; gap junctions); (E) mNeonGreen-EB3-N-7 (human microtubule-associated protein; RP/EB family); (F) mNeonGreen-Keratin-N-17 (human; intermediate filaments; cytokeratin 18); (G) mNeonGreen-Lamin B1-N-18 (human; nuclear envelope); (H) mNeonGreen-Lifeact-N-7 (yeast; actin); (I) mNeonGreen-MANNII-N-10 (mouse mannosidase 2; endoplasmic reticulum); (J) mNeonGreen-MyosinIIA-N-14 (mouse non muscle; actin binding); (K) mNeonGreen-Nup50-N-10 (human; nuclear pore complex); (L) mNeonGreen-PDHA1-N-10 (human pyruvate dehydrogenase; mitochondria); (M) mNeonGreen-PMP-N-10 (human peroxisomal membrane protein; peroxisomes); (N) mNeonGreen-MAPTau-N-10 (human microtubule associated protein); (O) mNeonGreen-TFR-N-20 (human transferrin receptor; plasma membrane); (P) mNeonGreen-TPX2-N-10 (human; microtubules); (Q) mNeonGreen-VASP-N-10 (mouse; focal adhesions); (R) mNeonGreen-VE-Cadherin-N-10 (human; adhesion junctions); (S) mNeonGreen-Vimentin-N-7 (human; intermediate filaments); (T) mNeonGreen-Zyxin-N-6 (human; focal adhesions). The cell line used for expression N-terminal mNeon-Green constructs was human cervical adenocarcinoma cells (HeLa-S3; ATCC, CCL-2.2) in panels F, K, P and S. HeLa CCL2 (ATCC) cells were used in the remaining panels. Scale bars represent 10 µm.

Figure 7:
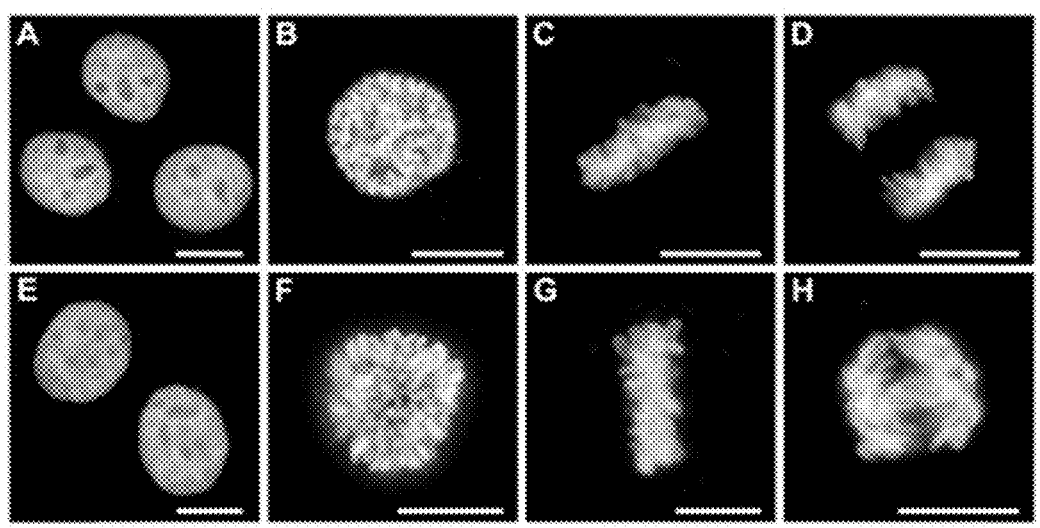

FIG. 7. Fluorescence imaging of mNeonGreen H2B fusion vectors. (A)-(D) C-terminal mNeonGreen-H2B-C-10 (human) in HeLa S3 cells; (A) interphase; (B) prophase; (C) metaphase; (D) anaphase; (E)-(H) N-terminal mNeonGreen-H2B-N-6 (human) in HeLa S3 cells; (E) interphase; (F) prophase; (G) metaphase; (H) anaphase. Scale bars represent 10 µm.

Figure 8:
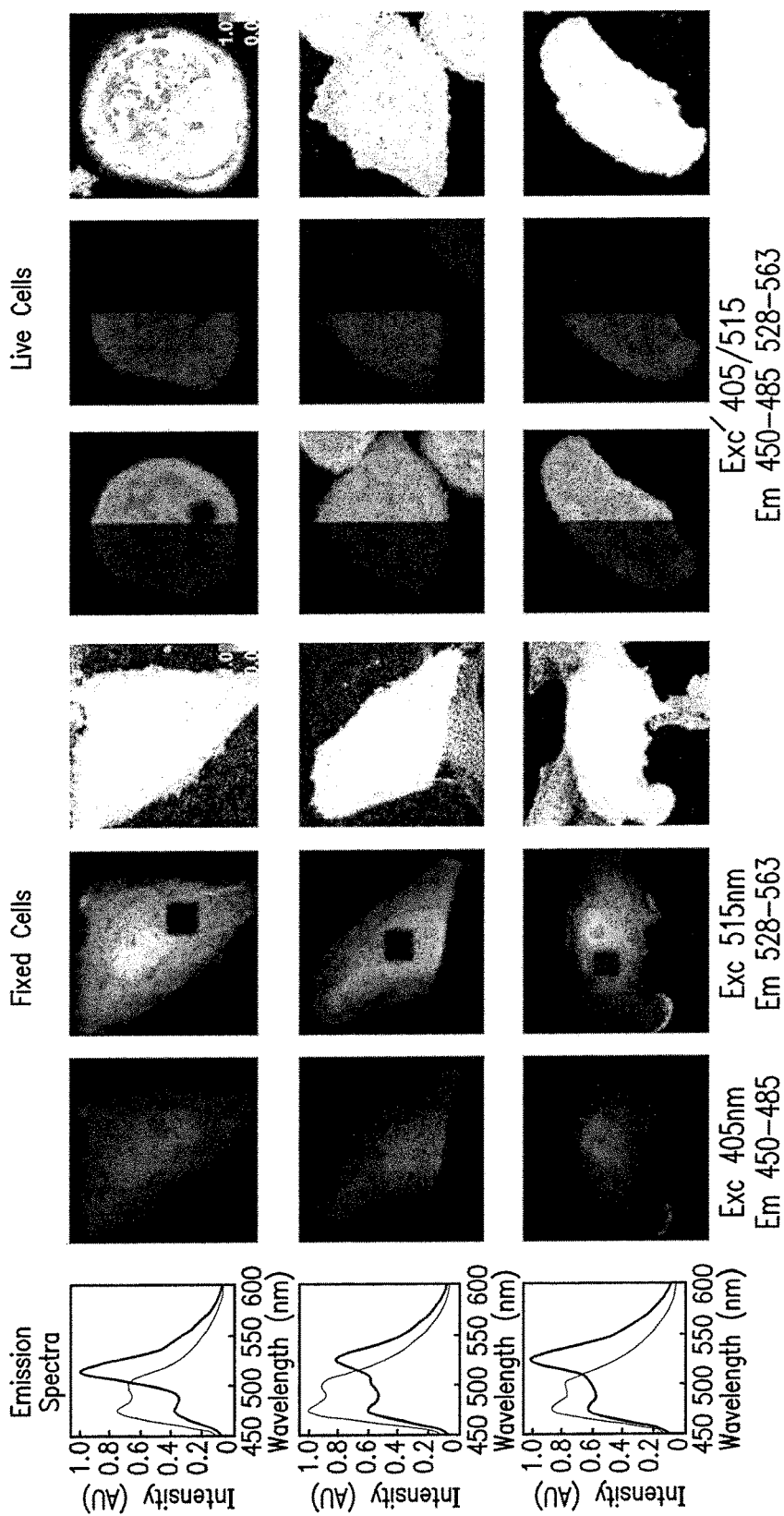

FIG. 8. Sample FRET experiments. (A) Emission spectra and fixed and live cell FRET images for (A) mTurquoise-mNeonGreen, (B) mTurquoise-mVenus, and (C) mCerulean-mVenus. Fixed Cells. The first column is the post-AP image of donor with 405 nm excitation illustrating increase in donor image intensity after bleaching an ROI. The second column is the post-AP image of acceptor with 515 nm excitation illustrating the same region has been photobleached. The third column is a ratiometric image of the donor to represent the increase in intensity of the bleached region, which is representative of FRET efficiency (see FRET Efficiency Bar below). Live Cells. The first column is the pre-AP image of both the donor and acceptor, with each taking up half of the total image. The second column is the post-AP image of the donor and acceptor showing the increase in intensity of the donor and that the acceptor was photobleached. The third column is a ratiometric image of the donor to represent the increase in intensity of the bleached cell, which is representative of FRET efficiency (see FRET Efficiency Bar below). FRET Efficiency Bar. Placed on the ratiometric image of a cell with a bleached region (Fixed cells) or an entire bleached cell (Live cells). Blue-green represents an average FRET efficiency of ~0 and Pink-white is approaching 1.

DETAILED DESCRIPTION OF THE INVENTION

When describing the present invention, all terms not defined herein have their common meanings recognized in the art. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention.

As used herein, typical monomerization required a known or a previously solved crystalline structures of the target fluorescent protein or a very close homolog thereof as a starting template. Certain monomeric fluorescent proteins have been generated without the use of solved crystal structures, but these cases have relied on relatively close homology of predicted tetramer interface residues with fluorescent proteins whose structures were already known

[9,10] (for example, mAG was engineered from Azami-Green based on ~52% peptide sequence identity (~74% positive) to DsRed over the full length of the protein). The cephalochordate fluorescent proteins are evolutionarily distant from other known fluorescent proteins [11], with LanYFP displaying <40% sequence identity to fluorescent proteins from all other classes of organism, and only 20% homology (~42% positive) to the closest homolog which has been monomerized (Kusabira-Orange [12]). No structure has yet been solved for a cephalochordate fluorescent protein. One exemplary compositions derived from such method as described herein was designated as monomeric NeonGreen (mNeonGreen) SEQ ID NO: 1.

In another embodiment, the disclosure provides a nucleic acid sequence encoding a polypeptide that has at least about 95% homology with the polypeptide encoded by the nucleic acid of SEQ ID NO: 2. It is well understood by those of skill in the art that in many instances modifications in particular locations in the polypeptide sequence may have no effect upon the properties of the resultant polypeptide. Unlike the specific mutations described in detail herein, other mutations provide polypeptides which have properties essentially or substantially indistinguishable from those of the specific polypeptides disclosed herein (U.S. Pat. No. 6,800,733, which is incorporated herein by reference). In the case represented in U.S. Pat. No. 6,800,733, it was accepted that amino acid sequence of "a modified form of an Aequorea wild-type GFP polypeptide is at least 95% homologous to the amino acid sequence" with a disclosed core protein sequence including key amino acids specified is within the genus of disclosed protein molecules.

In yet another embodiment, a nucleic acid present in other than its natural environment, wherein said nucleic acid encodes a green/yellow chromoprotein or fluorescent mutant thereof, and wherein said nucleic acid has a sequence identity of at least about 90% with SEQ ID NO: 2. Variations of nucleic acid sequences that are at least about 90% homologues that encode a chromo- or fluorescent protein were accepted as within the defined genus (U.S. Pat. No. 7,166,444, which is incorporated herein by reference).

In one aspect of the current disclosure, the inventors utilized the I-TASSER server [13] to generate a theoretical tertiary structure for LanYFP. The top structure generated by I-TASSER was then used to model the tetramer structure by aligning with known structures for tetrameric fluorescent proteins, including dsFP483 (a cyan fluorescent protein from *Discosoma* sp. [14]), which was predicted by I-TASSER to be one of its closest tetrameric structural relatives. Starting configurations of the A/B and A/C dimers based on these structural alignments were then used as input to the RosettaDock algorithm [15], and several of the lowest energy configurations predicted by RosettaDock were used for selection of side chains to target for monomerization (FIG. 2).

In another aspect, the wild-type LanYFP gene was modified by appending the first and last 7 amino acids of EGFP to the N and C termini of the coding sequence, respectively, as has become common practice with new fluorescent proteins [7], as well as an additional 4 amino acid linker sequence (DNMA) before the N-terminus of the original protein coding sequence. This arrangement tends to improve folding and localization of many fusions for many fluorescent proteins. Next, the inventors planned a strategy based on the reliable paradigm of first breaking the weaker (hydrophilic) A/B interface, rescuing fluorescence of the resulting dimer by directed evolution, then breaking the stronger (hydrophobic) A/C interface of the resulting bright dimer, and finally rescuing the fluorescence of the monomer. This strategy was highly successful in generating a monomeric variant of LanYFP based on our structural models.

The present disclosure provides a method that indicated in order to break the A/B interface of LanYFP, mutations I118K, which was predicted to introduce a positive charge in near the center of the predicted interface, and N174T which was expected to improve folding, were accordingly created by molecular biology methods. As expected, these mutations gave rise to a variant with substantially reduced fluorescence but which migrated as a dimer on a non-denaturing SDS-PAGE gel. Additional rounds of directed evolution led to a bright dimeric variant, designated dLanYFP, with the additional mutations A45D, S163N, and V171A, whose optical properties are nearly identical to those of the parental tetramer (see Table 1). This exemplary mutant was selected as the starting point for developing the monomer.

The disclosure also indicated that in order to break the dLanYFP A/C interface, the mutation D156K was initially selected to introduce a positive charge close to the center of the predicted interface. This mutant was almost entirely non-fluorescent, but could be rescued through several rounds of directed evolution, with final mutations Q56H, F67Y, S100T, F115A, T141S, and T158S. The resulting variant, however, appeared to migrate only partially as a monomer on non-denaturing SDS-PAGE, and almost entirely as a dimer in size exclusion chromatography. To introduce additional positive charge at the A/C interface and eliminate hydrophobic interactions, the inventors next constructed a library incorporating the additional mutations V140K/R and L144S/T/N, which the models used by the inventors predicted to form the remaining hydrophobic patch of the A/C interface. From this library, several fluorescent (but dimmer) clones were identified, all of which migrated entirely as monomers by size exclusion chromatography. Several additional rounds of directed evolution eventually generated a monomeric clone whose extinction coefficient and quantum yield approach the values of the original tetramer.

In one embodiment, the final mutant, designated mNeonGreen, contains a total of 21 mutations relative to tetrameric LanYFP (F15I, R25Q, A45D, Q56H, F67Y, K79V, S100V, F115A, I118K, V140R, T141S, M143K, L144T, D156K, T158S, S163N, Q168R, V171A, N174T, I185Y, F192Y), in addition to the appended EGFP-type termini. Based on our models, these mutations are distributed over the AB interface (I118K and N174T), the A/C interface (V140R, L144T, D156K, T158S, Q168R, and F192Y), additional external regions (R25Q, A45D, and S163N), and internal to the beta-barrel (F15I, Q56H, F67Y, K79V, S100V, F115A, T141S, M143K, V171A, and I185Y). A sequence alignment of LanYFP, dLanYFP, and mNeonGreen can be found in the FIG. 4. The monomeric status of the final clone was verified by size exclusion chromatography (FIG. 2).

In one embodiment of the disclosure, mNeonGreen displays sharp excitation and emission peaks (506 nm and 517 nm, FIG. 3 and Table 1) somewhat blue-shifted relative to the original tetrameric LanYFP, placing it roughly midway between typical GFP and YFP wavelength classes. As such, it was imaged quite efficiently using standard GFP bandpass or long pass filter sets, or separated from CFP signals with YFP filter sets. mNeonGreen is also among the brightest monomeric fluorescent proteins yet described. Its high quantum yield and extinction coefficient (Table 1) make it between 1.5 and 3 times as bright as commonly used GFPs and YFPs. Its photostability is slightly higher than that of mEGFP under widefield illumination (see Table 1), but somewhat lower for laser illumination (~C40% of mEGFP), within a practical range for imaging applications. Its fluorescence pKa of ~5.7 is similar to most modern GFPs and YFPs. mNeonGreen does not display any measurable sensitivity to Cl-ions.

In one aspect of the invention, in order to determine the performance of mNeonGreen as a fluorescent probe in live cell imaging, fusion vectors were constructed to both the N and C terminus of the fluorescent protein. All fusions localized as expected and mNeonGreen exhibited character typical of monomeric fluorescent proteins in "difficult" fusions, including histone H2B, connexins 26 and 43, and α-tubulin (FIGS. 5, 6, and 7). Fusions of mNeonGreen with signal peptides and targeting proteins confirmed expected localization patterns in the cytoskeleton (β-actin, Lifeact, fascin, cortactin, plastin (fimbrin), MAP Tau, light chain myosin, myosin IIA, EB3, TPX2 and myotilin), intermediate filaments (keratin and vimentin), the Golgi complex (sialyl-transferase, gal-T and mannosidase II), the nuclear envelope (lamin B1), nuclear pores (Nup50), nucleus (CAF1), endoplasmic reticulum (calnexin and calreticulin), the plasma membrane (annexin A4, CAAX, transferrin receptor, and C-src) nucleoli (fibrillarin), mitochondria (pyruvate dehydrogenase and TOMM20), endosomes (Rab4a, Rab5a, and RhoB GTPase), autophagosomes (LC3), centromeres (CENPB), tight junctions (β-catenin, VE-cadherin, and ZO1), DNA replication foci (PCNA) lysosomes (LAMP1), auto peroxisomes (peroxisomal membrane protein), various vesicles (clathrin and caveolin), and focal adhesions (α-actinin, talin, focal adhesion kinase, filamin A, VASP, paxillin, vinculin and zyxin). All phases of mitosis were observed in fusions of human histone H2B to either the N or C terminus of mNeonGreen (FIG. 7).

In one specific embodiment of the current invention, because of its high extinction coefficient and quantum yield, it was expected that mNeonGreen would be a good FRET acceptor for cyan fluorescent proteins. Most notably in the tests of this property, a direct fusion of mNeonGreen to mTurquoise produced higher FRET efficiency than the same construct using mVenus as the acceptor (50% versus 41% as measured by acceptor photobleaching; 55% versus 43% as measured by fluorescence lifetime imaging (FLIM), see, for example, FIG. 8). Thus, in one embodiment of the invention, mNeonGreen can be used as an excellent choice as FRET acceptor for many applications.

The present disclosure demonstrates that precise structural characterization is not required for successful monomerization of a novel fluorescent protein. Though LanYFP has very low sequence identity to any fluorescent protein whose structure has been solved, modeling of its tetrameric configuration utilizing structure prediction and protein-protein docking algorithms provided sufficient information to identify the side chains to target for monomerization.

In one embodiment, the resulting monomeric variant, mNeonGreen, has optical properties which are superior to those of the most commonly used green and yellow fluorescent proteins, and shows especially good promise as a FRET acceptor.

In another embodiment, since it shares so little sequence identity with other commonly used fluorescent proteins, mNeonGreen are useful target for antibody development, and are amenable to orthogonal co-IP experiments along with jellyfish and coral-derived fluorescent proteins.

The disclosed computation-based approach to fluorescent protein engineering should open up possibilities for monomerizing many additional oligomeric fluorescent proteins with potentially superior optical properties whose structures have not yet been solved.

SEQ ID NO: 1
MVSKGEEDNMASLPATHELHIFGSINGVDFDMVGQGTGNPNDGYEELNLK

STKGDLQFSPWILVPHIGYGFHQYLPYPDGMSPFQAAMVDGSGYQVHRTM

QFEDGASLTVNYRYTYEGSHIKGEAQVKGTGFPADGPVMTNSLTAADWCR

SKKTYPNDKTIISTFKWSYTTGNGKRYRSTARTTYTFAKPMAANYLKNQP

MYVFRKTELKHSKTELNFKEWQKAFTDVMGMDELYK

SEQ ID NO: 2
Atggtgagcaagggcgaggaggataacatggcctctctcccagcgacaca tgagttacacatctttggctccatcaacggtgtggactttgacatggtgg gtcagggcaccggcaatccaaatgatggttatgaggagttaaacctgaag tccaccaagggtgacctccagttctcccctggattctggtccctcatat cgggtatggcttccatcagtacctgccctaccctgacgggatgtcgcctt tccaggccgccatggtagatggctccggataccaagtccatcgcacaatg cagtttgaagatggtgcctcccttactgttaactaccgctacacctacga gggaagccacatcaaaggagaggcccaggtgaaggggactggtttccctg ctgacggtcctgtgatgaccaactcgctgaccgctgcggactggtgcagg tcgaagaagacttaccccaacgacaaaaccatcatcagtacctttaagtg gagttacaccactggaaatggcaagcgctaccggagcactgcgcggacca cctacacctttgccaagccaatggcggctaactatctgaagaaccagccg atgtacgtgttccgtaagacggagctcaagcactccaagaccgagctcaa cttcaaggagtggcaaaaggcctttaccgatgtgatgggcatggacgagc tgtacaagtaa

TABLE 1

Physical and optical characteristics of *Branchiostoma lanceolatum*-derived fluorescent proteins described here, and other green and yellow fluorescent proteins in common usage.

| Protein | Ex (nm) | Em (nm) | ε† | φ‡ | Brightness (% EGFP) | Photostability¶ | pKa§ | Oligomerization |
|---|---|---|---|---|---|---|---|---|
| LanYFP | 513 | 524 | 150,000 | 0.95 | 424 | ND | 3.5 | tetramer |
| dLanYFP | 513 | 524 | 125,000 | 0.90 | 335 | ND | ND | dimer |
| mNeonGreen | 506 | 517 | 115,000 | 0.80 | 274 | 158 | 5.7 | monomer |
| mCitrine# | 516 | 529 | 77,000 | 0.76 | 174 | 49 | 5.7 | monomer |
| mVenus# | 515 | 528 | 92,200 | 0.57 | 156 | 15 | 6.0 | monomer |
| EYFP# | 514 | 527 | 83,400 | 0.61 | 151 | 60 | 6.9 | weak dimer |

TABLE 1-continued

Physical and optical characteristics of *Branchiostoma lanceolatum*-derived fluorescent proteins described here, and other green and yellow fluorescent proteins in common usage.

| Protein | Ex (nm) | Em (nm) | ε† | φ‡ | Brightness (% EGFP) | Photostability¶ | pKa§ | Oligomerization |
|---------|---------|---------|------|------|---------|---------------|------|-----------------|
| mEmerald# | 487 | 509 | 57,500 | 0.68 | 116 | 101 | 6.0 | monomer |
| mEGFP# | 488 | 507 | 56,000 | 0.60 | 100 | 150 | 6.0 | monomer |

Data as reported previously[2, 16];
†Molar extinction coefficient ($M^{-1}cm^{-1}$) determined by alkali denaturation method[16];
‡Fluorescence quantum yield (see Methods);
¶Half-time for photobleaching under widefield illumination starting from 1000 photons/s emitted per fluorescent protein chromophore, as measured in live cells (see Methods)[8, 17].
ND = not determined.

EXAMPLES

Example 1—Modeling

The primary amino acid sequence of wild-type LanYFP (b1FP-Y3, GenBank accession ACA48232) was used as input to the I-TASSER structure prediction server (Roy, A., Kucukural, A. & Zhang, Y. I-TASSER: a unified platform for automated protein structure and function prediction. *Nature Protocols* 5, 725-738 (2010).) using default parameters. The top-scoring structure returned by I-TASSER was aligned to the published tetramer crystal structure of dsFP483 (PDB ID 3CGL) [19] to create two dimer configurations, which were designated "A/B" and "A/C" for the homologous DsRed dimer configurations [20,21] PDB files containing these starting dimer configurations were used as input to the RosettaDock server (Lyskov, S. & Gray, J. J. The Rosetta-Dock server for local protein-protein docking. *Nucleic Acids Res* 36, W233-8 (2008).) using default parameters. Several of the lowest energy configurations returned by the RosettaDock server for each dimer interface were used to identify the side chains most likely to be involved in critical dimer interactions.

Example 2—Cloning, Protein Expression, and Purification

All fluorescent protein coding sequences were inserted between BamHI and EcoRI sites in the constitutive expression vector pNCS which encodes an N-terminal 6×His tag and linker Fluorescent proteins were expressed in *E. coli* strain NEBTurbo (New England Biolabs) or Mach1 (Invitrogen) by growing cultures in 2×YT medium supplemented with ampicillin overnight at 37° C. and shaking at 250 rpm. Fluorescent proteins were purified by Ni2+-affinity chromatography as previously described1. Proteins were eluted in 50 mM Tris pH 7.5 or 50 mM sodium phosphate buffer pH 7.5 containing 250 mM imidazole. For all further characterization experiments, eluted fluorescent proteins were buffer-exchanged using Amicon Ultra0.5 10 kD MWCO ultrafiltration units (Millipore) into the same buffer without imidazole. Proteins were found to be stable when stored at 4° C. indefinitely or when frozen at −20° C. or −80° C.

Example 3—Directed Evolution

Multiple rounds of directed evolution and screening were performed as previously described [23,24], with a summary of techniques following here. Screening of FP-expressing *E. coli* colonies was done by eye using a blue LED lamp and longpass yellow filter. For each round of directed evolution, one to three of the brightest clones from the previous round of were used as the template for construction of randomly mutagenized libraries using the GeneMorph II kit (Agilent Technologies). Mutagenic PCR conditions were chosen such that the library would contain an average of 2 to 4 mutations per clone. 20 to 30 of the brightest clones identified by random mutagenesis were sequenced, and any clones containing mutations predicted to revert the oligomeric state of the protein were rejected. The remaining amino acid positions identified by random mutagenesis were partially or fully randomized by directed mutagenesis by overlap extension PCR using degenerate primers, with library sizes typically between 500 and 25,000 unique clones. The brightest clones from directed mutagenesis were sequenced, optically characterized, and evaluated for their oligomeric state by size exclusion chromatography. Those clones which possessed superior optical properties while maintaining the desired oligomeric state were used as the input for the next round of directed evolution.

Example 4—Optical Characterization

For spectroscopy measurements, all samples and buffers were filtered or centrifuged immediately before use. Purified fluorescent protein (FP) samples were diluted into 10 mM Tris, pH 7.4 buffer and fluorescein (F2−; Sigma, St. Louis, Mo.) was diluted into 0.1M NaOH. Absorbance measurements were collected with a Cary Bio 100 UV-Vis Spectrophotometer (Varian Inc., Walnut Creek, Calif.). Fluorescence measurements were collected with a Cary Eclipse Spectrophotometer (Varian Inc.). All measurements for absorbance were immediately preceded with a measured baseline with the appropriate blank buffer. Fluorescence pKa values were determined by measuring fluorescence emission of heavily diluted purified dialyzed fluorescent protein samples in 100 mM mixed citrate-Tris-glycine buffer with pH ranging from 3 to 11.

Example 5. Size Exclusion Chromatography

Purified and dialyzed fluorescent protein samples were diluted into 50 mM Tris-HCl pH 7.5, 100 mM NaCl and filtered through 0.2 μm filters immediately prior to injection into a Shimadzu Nexera UHPLC equipped with a Waters BEH200 1.7 μm 4.6×150 mm size exclusion column and 4.6×30 mm guard column. Samples were run in the same buffer at a flow rate of 0.3 ml per minute for a total run time of 20 minutes. Fluorescence of the eluted protein was detected with an RF-20Axs fluorescence detector (Shimadzu) with 480 nm and 540 nm excitation and 530 nm and 620 nm emission wavelengths. Each LanYFP or variant sample was co-injected with mCherry [24], which had been purified under identical conditions and which served as a monomeric size standard. A control run of mCherry alone displayed no bleedthrough into the yellow emission channel.

Example 6. Quantum Yield ($\varphi$) and Extinction Coefficient ($\varepsilon$)

A relatively concentrated stock sample of FP or F2– was prepared and its full absorbance spectrum was measured with 0.5 nm step size. This was done in the same cuvette to be used for fluorescence spectra measurement. Identically absorbing solutions (target OD≤0.05) were separately prepared in quadruplicate for the FP and F2– ($\varphi$=0.925) [25] and their emission spectra were measured with 488 nm excitation. The excitation and emission bandwidths were 2.5 nm and 5 nm, respectively with 1.0 nm step size. Emission was collected for 490-750 nm and the integrated intensities for each sample were calculated using the fluorimeter's software. The average integrated intensities and their associated absorbance values were used to calculate quantum yields as previously described [24].

Absorbance spectra of purified FP samples were measured in quadruplicate (0.5 nm step size) and were used to determine the mean peak absorbance value. A baseline absorbance spectrum was then measured with buffer diluted 1:1 with 2M NaOH (1M final concentration). A double-concentration sample was prepared in half the cuvette volume, mixed 1:1 with 2M NaOH, and its absorbance was immediately measured. Data was acquired for NaOH-denatured protein between 430 and 460 nm (with a peak ~447 nm) and a full UV-Vis spectrum was measured for the last sample to ensure the protein fully denatured. Extinction coefficients were determined as described previously [26, 27], assuming that the denatured chromophore absorbed with an extinction coefficient equivalent to a denatured avGFP chromophore (44,000 M-1 cm-1).

Example 7. Excitation and Emission

For excitation spectra, fluorescence emission was monitored at 535 nm. For emission spectra, fluorescence excitation was 465 nm with a 5.0 nm bandpass throughout.

Example 8. Photobleaching

Laser-scanning confocal and widefield microscopy photobleaching experiments utilized fusions of the appropriate fluorescent protein to human histone H2B to allow for localized fluorescence in the nucleus. HeLa S3 cells were cultured in Dulbecco's modified Eagle's medium (DMEM; Invitrogen) supplemented with 12.5% fetal bovine serum (FBS; HyClone). The cells were then seeded onto 35 mm Delta T imaging dishes (Bioptechs) for live cell imaging. Approximately 24 hours after being seeded, cells were then transfected with 1 µg of DNA using Effectene (Qiagen) and maintained in a 5% CO2 incubator for at least 24 hours before imaging.

Widefield photobleaching was performed on a Nikon TE2000 inverted microscope equipped with a Nikon Plan Fluorite 40× dry objective (NA=0.85) and an X-Cite Exacte metal halide lamp (Lumen Dynamics, Mississauga, Ont). Photobleaching was conducted using a Brightline FITC-HYQ filter cube (Chroma, Bellows Falls, Vt.) and a Newport 1918-C (Newport, Rochester, N.Y.) optical power meter was used to verify that the illumination power at the objective was 4.3 mW. Power moderation was achieved by using neutral density filters contained within the lamp. With neutral density (ND32) in place, a region containing 10-20 evenly bright nuclei was located. The neutral density was then removed from the light path and the region was photobleached continuously with a 65 ms exposure time for 15 minutes for a total of 4700 frames. Images were collected with a QImaging Retiga EXi camera (Photometrics, Tucson, Ariz.). Multiple regions were photobleached to ensure that data for 30 nuclei could be averaged. The raw data was collected using NIS-Elements software (Nikon) and then analyzed with Simple PCI software (Hamamatsu, Hamamatsu City, Japan).

Confocal photobleaching measurements were collected on an Olympus FV1000 confocal microscope with an Olympus PLAPO 40× oil-immersion objective (NA=1.0). A 488 nm Argon-ion laser line (Melles Griot, Albuquerque, N. Mex.) was confirmed to be attuned to an output power of 1005 µW at the objective with a FieldMax II-TO power meter (Coherent, Santa Clara, Calif.). The microscope was set to a zoom of 2×, a pinhole size of 500 µm, a photomultiplier voltage of 450V, an offset of 8, and a scan time of 4 µs/pixel. Emission was collected with detector slit settings of 505-605 nm. Utilizing an output of minimum laser power, a region of evenly bright nuclei was located. The laser power was raised back to 1005 µW and each region was photobleached continuously for ~8 minutes for a total of 300 frames, with multiple regions being bleached to ensure data for 30 nuclei. Raw data was collected with the FluoView software (Olympus) and then analyzed with Simple PCI software (Hamamatsu).

All photobleaching data were scaled to represent the equivalent of an emission rate of 1000 photons/s per fluorescent protein chromophore at time zero as previously described6,11, a condition which produces a half-time of 150s for EGFP.

Example 9. Acceptor Photobleaching FRET (AP FRET)

FRET constructs of mTurquoise-mNeonGreen, mTurquoise-mVenus and mCerulean-mVenus all contained a 10 amino acid linker -SGLRSPPVAT between FPs12. All acceptor photobleaching measurements were performed on an Olympus FV 1000 confocal microscope with a UPLAPO 40× oil immersion objective (NA=1.0). A 515 nm Ar-ion laser line was used with a 458/515 dichroic mirror to excite and photobleach the mNeonGreen or mVenus in each FRET pair. Emission during acceptor photobleaching was collected in one channel spanning 528-553 nm to ensure bleaching of all fluorescence. For each of the FRET constructs, a 405 nm diode laser line was used with a 405/488 dichroic for excitation of the CFP with one emission channel spanning 450-485 nm. The detector gain was set to 685 volts, the offset was set to 8 and the scan speed was set to 8.0 µs/pixel. Each experiment was performed with a pinhole size of 500 µm.

For FRET efficiency measurements in live cells, a full view image of the donor was acquired before and after acceptor photobleaching of the entire cell. A region of interest (ROI) was drawn over identical areas of the cell in each image and the average intensities of these regions were calculated using the microscope's software. The following formula was used to calculate the FRET efficiency of each construct: FE=1-(Average intensity donor PreAP/Average intensity donor PostAP) [29]

For FRET efficiency measurements in fixed cells, a full view image of the donor was acquired before and after acceptor photobleaching. An ROI was drawn over an evenly bright part of the cell and acceptor photobleached. The average intensities of these regions were calculated using the microscope's software and the above FE formula was again used to calculate FRET efficiency.

Example 10. Frequency Domain Fluorescence Lifetime Measurements (FD-FLIM)

The fluorescence lifetime measurements were made using a ISS ALBA FastFLIM system (ISS Inc., Champaign, Ill.) coupled to an Olympus IX71 microscope equipped with a 60×/1.2 NA water-immersion objective lens. A Pathology Devices (Pathology Devices, Inc.) stage top environmental control system maintains temperature at 36° C. and CO2 at 5%. A 5 mW 448 nm diode laser was modulated by the FastFLIM module of the ALBA system at the fundamental frequency of 20 MHz13. The modulated laser is coupled to the ALBA scanning system, which is controlled by the VistaVision software (ISS Inc., Champaign, Ill.). The fluorescence signals emitted from the specimen are routed by a beam splitter through the 530/43 nm (acceptor emission) and the 480/40 (donor emission) band-pass emission filters. The signals are then detected using two identical avalanche photodiodes (APD). The phase delays and modulation ratios of the emission relative to the excitation are measured at seven modulation frequencies (20, 40, 60, 80, 100, 120, 140 MHz) for each pixel of an image.

The system is calibrated with the 50 μM Coumarin 6 dissolved in ethanol (lifetime 2.5 ns) to provide the software with a reference standard to estimate the lifetime values from the experimental data [30]. Additionally, a second reference standard, 10 mM HPTS (8-hydroxypyrene-1,3,6-trisulfonic acid) dissolved in phosphate buffer (PB) pH 7.8 (lifetime of 5.4 ns) is used to check that the system is accurately reporting the fluorescence lifetime of a known sample. The distribution of the lifetimes for all the pixels in the image is determined using the phasor (polar) plot method [31'32]. For live-cell imaging, transfected cells grown in chambered coverglass (2 well, Thermo Scientific) were identified by epifluorescence microscopy, and then imaged by FD-FLIM using the 448 nm laser line. The laser power was adjusted to achieve approximately 100,000 counts per second in the donor emission channel, and frame averaging was used to accumulate approximately 200 peak counts per pixel. The data were analyzed with the VistaVision software (ISS Inc., Champaign, Ill.) using a region average for each selected square region of interest (ROI, typically 1-2 μm).

Example 11. Fusion Plasmid Construction mNeonGreen fluorescent protein expression vectors were constructed using C1 and N1 (Clontech-style) cloning vectors. The mNeonGreen cDNA was amplified with a 5' primer encoding an AgeI site and a 3' primer encoding either a BspEI (C1) or NotI (N1) site for generating cloning vectors to create C-terminal and N-terminal fusions (with regards to the FP), respectively. Purified and digested PCR products were ligated into similarly digested EGFP-C1 and EGFP-N1 cloning vector backbones. To obtain targeting fusion vectors, the appropriate cloning vector and a previously assembled EGFP or mEmerald fusion vector were digested, either sequentially or doubly, with the appropriate enzymes and ligated together after gel purification.

Thus, to prepare mNeonGreen C-terminal fusions (number of linker amino acids in parenthesis), the following digests were performed: annexin A4 (12), NheI and BspEI (Alen Piljic, EMBL, Heidelberg, Germany; NM_001153.3); β-actin (7), NheI and BglII (human β-actin cDNA source: Clontech, Mountain View, Calif.; NM_001101.3); β-catenin (20), XhoI and BamHI (mouse β-catenin cDNA source: Origene, Rockville, Md.; NM_001165902.1); 20 amino acid farnesylation signal from c-Ha-Ras (CAAX; 5), AgeI and BspEI (c-Ha-Ras cDNA source: Clontech, Mountain View, Calif.; NM_001130442.1); CAF1 (10), AgeI and BspEI (mouse chromatin assembly factor cDNA source: Akash Gunjan, Florida State University; NM_013733.3); caveolin 1 (10), NheI and BglII (human caveolin 1 cDNA source: Origene; NM_001753); endosomes (14), NheI and BspEI (endosomes cDNA source: Clontech; NM_004040.2); fascin (10), BspEI and BamHI (human fascin cDNA source: Origene; NM_003088.2); fibrillarin (7), AgeI and BspEI (fibrillarin cDNA source: Evrogen, Moscow, Russia; NM_001436.3); filamin A (14), BspEI and HindIII (human filamin cDNA source: David Calderwood, Yale University; NM_001456.3); human lysosomal membrane glycoprotein 1 (20), BamHI and NotI (LAMP1; George Patterson, NIH, Bethesda Md., U.S.A.; NM_012857.1); human light chain clathrin (15), NheI and BglII (human clathrin light chain cDNA source: George Patterson, NIH; NM_001834.2); human myotilin, AgeI and BspEI (MYOT; Origene; NM_006790.1); PCNA (19), AgeI and BspEI (proliferating cell nuclear antigen cDNA source: David Gilbert, FSU; NM_002592.2); plastin (10), BspEI and XhoI (human plastin 1 (fimbrin) cDNA source: Origene; NM_002670.1); canine Rab4a, BglII and BamHI (Rab4a cDNA source: Viki Allen, U. Manchester, UK; NM_004578.2); LC3B (7), AgeI and BspEI (rat LC3B cDNA source: Jenny M. Tam, Harvard University; U05784.1); talin (22) AgeI and BspEI (mouse talin 1 cDNA source: Clare Waterman, NIH; NM_011602.5); α-tubulin (18), NheI and BglII (human α-tubulin cDNA source: Clontech, Mountain View, Calif.; NM_006082).

To prepare mNeonGreen N-terminal fusions (number of linker amino acids in parenthesis), the following digests were performed: human non-muscle α-actinin, EcoRI and NotI (cDNA source, Tom Keller, Florida State University (FSU), Tallahassee, Fla., U.S.A.; NM_001130005.1); human calnexin, AgeI and NotI (Origene; NM_001746.3); c-src (7), BamHI and EcoRI (chicken c-src cDNA source: Marilyn Resh, Sloan-Kettering, New York; XM_001232484.1); connexin-43 (7), BamHI and NotI (rat Cx43 cDNA source: Matthias Falk, Lehigh U; NM_001004099.1); EB3 (7), BglII and BamHI (EB3 cDNA source: Lynne Cassimeris, Lehigh University; NM_012326.2); human keratin 18, EcoRI and NotI (Open Biosystems, Huntsville, Ala., U.S.A.; NM_199187.1); lamin B1 (10), EcoRI and BamHI (human lamin B1 cDNA source: George Patterson, NIH; NM_005573.2); Lifeact (7), BamHI and NotI (Lifeact cDNA source: IDT, Coralville, Iowa); mouse mannosidase 2 (112 N-terminal amino acids, MAN-NII; 10), NheI and BamHI (cDNA source: Jennifer Lippincott-Schwartz, NIH; NM_008549.2); myosin IIA (14) NheI and BglII (mouse myosin IIA cDNA source: Origene; NM_022410.2); human nucleoporin 50 kDa, BamHI and NotI (NUP50 cDNA source: Origene; NM_007172.2); human pyruvate dehydrogenase, AgeI and NotI (human PDHA1 cDNA source: Origene; NM_000284); human peroxisomal membrane protein, NotI and AgeI (PMP cDNA source: Origene; NM_018663.1); human MAP Tau (10), AgeI and NotI (MAP Tau cDNA source: Origene; NM_016841); human TfR (20), BamHI and NotI (transferrin receptor cDNA source: George Patterson, NIH; NM_NM_003234); human TPX2 (10), AgeI and NotI (TPX2 cDNA source: Patricia Wadsworth, University of Massachusetts, Amherst; NM_012112.4); mouse VASP (10), NheI and BamHI (cDNA source: Clare Waterman, NIH; NM_009499); vascular epithelial cadherin (10), AgeI and NotI (human VE cadherin cDNA source: Origene, Rockville, Md.; NM_001795.3), vimentin (7), BamHI and NotI (human vimentin cDNA source: Robert Goldman, Northwestern University; NM_003380.3), zyxin (6), BamHI and NotI (human zyxin cDNA source: Origene, Rockville, Md.; NM_003461). All DNA for transfection was prepared using the Plasmid Maxi kit (QIAGEN, Valencia, Calif.). To ensure proper localization, mNeonGreen fusion proteins were characterized by transfection in HeLa (S3 or CCL2 line) or MDCK cells (ATCC; Manassas, Va.) using Effectene (QIAGEN; Valencia, Calif.) and ~1 µg vector. Transfected cells were grown on coverslips in DMEM/F12, fixed after 48 hours, and mounted with Gelvatol. Epifluorescence images were captured with a Nikon 80i microscope using widefield illumination and a Chroma FITC filter set to confirm proper localization.

Example 12. Microscopy

All filters for fluorescence screening and imaging were purchased from Chroma Technology (Bellows Falls, Vt.), Omega Filters (Brattleboro, Vt.) or Semrock, Inc. (Rochester, N.Y.). HeLa epithelial (CCL-2, ATCC, Manassas, Va., U.S.A.) and grey fox lung fibroblast (CCL-168, ATCC) cells were grown in a 50:50 mixture of DMEM (Dulbecco's modified Eagle's medium) and Ham's F12 with 12.5% Cosmic calf serum (Thermo Scientific; Logan, Utah) and transfected with Effectene (QIAGEN). Imaging was performed in Delta-T culture chambers (Bioptechs; Butler, Pa.) under a humidified atmosphere of 5% CO2 in air. Imaging in widefield mode was performed with a Nikon (Melville, N.Y.) TE-2000 inverted microscope equipped with Omega QuantaMax™ filters and a Photometrics (Tucson, Ariz.) Cascade II camera or an Olympus IX71 inverted microscope equipped with Semrock BrightLine™ filters and a Hamamatsu (Bridgewater, N.J.) ImagEM™ camera. Laser-scanning confocal microscopy was conducted using a Nikon C1Si and an Olympus FV1000, both equipped with argon-ion (457 and 488 nm) and helium-neon or diode (543 and 561 nm respectively) lasers and proprietary filter sets. Spinning disk confocal microscopy was performed on an Olympus DSUIX81 equipped with a Lumen 200 illuminator (Prior Scientific; Boston, Mass.), a Hamamatsu 9100-13 EMCCD camera, Semrock filters and ten-position filter wheels driven by a Lambda 10-3 controller (Sutter). In some cases, cell cultures expressing fluorescent protein fusions were fixed after imaging in 2% (w/v) paraformaldehyde (Electron Microscopy Sciences; Hatfield, Pa.) and washed several times in PBS containing 0.05 M glycine before mounting with a polyvinyl alcohol-based medium.

REFERENCES

1. Tsien, R. Y. The green fluorescent protein. *Annu. Rev. Biochem.* 67, 509-544 (1998).
2. Shaner, N.C., Patterson, G. H. & Davidson, M. W. Advances in fluorescent protein technology. *J. Cell. Sci.* 120, 4247-4260 (2007).
3. Goedhart, J. et al. Structure-guided evolution of cyan fluorescent proteins towards a quantum yield of 93%. *Nat Comms* 3, 751 (2012).
4. Markwardt, M. L. et al. An Improved Cerulean Fluorescent Protein with Enhanced Brightness and Reduced Reversible Photoswitching. *PLoS ONE* 6, e17896 (2011).
5. Miyawaki, A. Development of probes for cellular functions using fluorescent proteins and fluorescence resonance energy transfer. *Annu. Rev. Biochem.* 80, 357-373 (2011).
6. Campbell, R. E. et al. A monomeric red fluorescent protein. *Proc Natl Acad Sci USA* 99, 7877-7882 (2002).
7. Shaner, N. C. et al. Improved monomeric red, orange and yellow fluorescent proteins derived from *Discosoma* sp. red fluorescent protein. *Nat Biotechnol* 22, 1567-1572 (2004).
8. Shaner, N. C. et al. Improving the photostability of bright monomeric orange and red fluorescent proteins. *Nature Methods* 5, 545-551 (2008).
9. Merzlyak, E. M. et al. Bright monomeric red fluorescent protein with an extended fluorescence lifetime. *Nature Methods* 4, 555-557 (2007).
10. Karasawa, S., Araki, T., Yamamoto-Hino, M. & Miyawaki, A. A green-emitting fluorescent protein from Galaxeidae coral and its monomeric version for use in fluorescent labeling. *J Biol Chem* 278, 34167-34171 (2003).
11. Li, G., Zhang, Q.-J., Zhong, J. & Wang, Y.-Q. Evolutionary and functional diversity of green fluorescent proteins in cephalochordates. *Gene* 446, 41-49 (2009).
12. Karasawa, S., Araki, T., Nagai, T., Mizuno, H. & Miyawaki, A. Cyan-emitting and orange-emitting fluorescent proteins as a donor/acceptor pair for fluorescence resonance energy transfer. *Biochem J* 381, 307-312 (2004).
13. Roy, A., Kucukural, A. & Zhang, Y. I-TASSER: a unified platform for automated protein structure and function prediction. *Nature Protocols* 5, 725-738 (2010).
14. Malo, G. D. et al. Crystal structure and Raman studies of dsFP483, a cyan fluorescent protein from *Discosoma striata*. *J Mol Biol* 378, 871-886 (2008).
15. Lyskov, S. & Gray, J. J. The RosettaDock server for local protein-protein docking *Nucleic Acids Res* 36, W233-8 (2008).
16. Shaner, N.C., Steinbach, P. A. & Tsien, R. Y. A guide to choosing fluorescent proteins. *Nature Methods* 2, 905-909 (2005).
17. Chalfie, M. & Kain, S. R. *Green Fluorescent Protein: Properties, Applications, and Protocols.* (Wiley-Interscience: Hoboken, N.J., 2006).
18. Roy, A., Kucukural, A. & Zhang, Y. I-TASSER: a unified platform for automated protein structure and function prediction. *Nature Protocols* 5, 725-738 (2010).
19. Malo, G. D. et al. Crystal structure and Raman studies of dsFP483, a cyan fluorescent protein from *Discosoma striata*. *J Mol Biol* 378, 871-886 (2008).
20. Campbell, R. E. et al. A monomeric red fluorescent protein. *Proc Natl Acad Sci USA* 99, 7877-7882 (2002).
21. Yarbrough, D., Wachter, R. M., Kallio, K., Matz, M. V. & Remington, S. J. Refined crystal structure of DsRed, a red fluorescent protein from coral, at 2.0-A resolution. *Proc Natl Acad Sci USA* 98, 462-467 (2001).
22. Lyskov, S. & Gray, J. J. The RosettaDock server for local protein-protein docking *Nucleic Acids Res* 36, W233-8 (2008).
23. Shaner, N. C. et al. Improving the photostability of bright monomeric orange and red fluorescent proteins. *Nature Methods* 5, 545-551 (2008).
24. Shaner, N. C. et al. Improved monomeric red, orange and yellow fluorescent proteins derived from *Discosoma* sp. red fluorescent protein. *Nat Biotechnol* 22, 1567-1572 (2004).

25. Magde, D., Wong, R. & Seybold, P. G. Fluorescence quantum yields and their relation to lifetimes of rhodamine 6G and fluorescein in nine solvents: improved absolute standards for quantum yields. *Photochemistry and Photobiology* 75, 327-334 (2002).
26. Gross, L. A., Baird, G. S., Hoffman, R. C., Baldridge, K. K. & Tsien, R. Y. The structure of the chromophore within DsRed, a red fluorescent protein from coral. *Proc Natl Acad Sci USA* 97, 11990-11995 (2000).
27. Chalfie, M. & Kain, S. R. *Green Fluorescent Protein: Properties, Applications, and Protocols.* (Wiley-Interscience: Hoboken, N.J., 2006).
28. Shaner, N.C., Steinbach, P. A. & Tsien, R. Y. A guide to choosing fluorescent proteins. *Nature Methods* 2, 905-909 (2005).
29. Subach, O. M., Cranfill, P. J., Davidson, M. W. & Verkhusha, V. V. An Enhanced Monomeric Blue Fluorescent Protein with the High Chemical Stability of the Chromophore. *PLoS ONE* 6, e28674 (2011).
30. Sun, Y., Day, R. N. & Periasamy, A. Investigating protein-protein interactions in living cells using fluorescence lifetime imaging microscopy. *Nature Protocols* 6, 1324-1340 (2011).
31. Colyer, R. A., Lee, C. & Gratton, E. A novel fluorescence lifetime imaging system that optimizes photon efficiency. *Microsc. Res. Tech.* 71, 201-213 (2008).
32. Redford, G. I. & Clegg, R. M. Polar plot representation for frequency-domain analysis of fluorescence lifetimes. *J Fluoresc* 15, 805-815 (2005).

The invention claimed is:

1. A non-naturally occurring isolated monomeric or dimeric lanYFP fluorescent protein comprising a polypeptide having at least 95% sequence identity to the amino acid sequence of SEQ ID NO: 1, wherein the protein comprises at least one mutation selected from the group consisting of: F15I, R25Q, A45D, Q56H, F67Y, K79V, S100V, F115A, I118K, V140R, T141S, M143K, L144T, D156K, T158S, S163N, Q168R, V171A, N174T, I185Y, and F192Y.

2. The non-naturally occurring lanYFP fluorescent protein of claim 1, wherein the protein is a monomer.

3. An isolated non-naturally occurring monomeric polypeptide encoded by a nucleic acid having at least 90% sequence identity to SEQ ID NO: 2 SEQ ID. No. 2, wherein the nucleotide sequence encodes for a polypeptide which comprises at least one mutation selected from the group consisting of: I118K or N174T, at least one mutation selected from the group consisting of: V140R, L144T, D156K, T158S, Q168R, and F192Y, and at least one mutation selected from the group consisting of: R25Q, A45D, S163N, F151, Q56H, F67Y, K79V, S100V, F115A, T141S, M143K, V171A, and I185Y.

4. The non-naturally occurring isolated monomeric or dimeric lanYFP fluorescent protein of claim 1, wherein the protein comprises at least one mutation selected from the group consisting of: I118K and N174T, at least one mutation selected from the group consisting of: V140R, L144T, D156K, T158S, Q168R, and F192Y, and at least one mutation selected from the group consisting of: R25Q, A45D, S163N, F151, Q56H, F67Y, K79V, S100V, F115A, T141S, M143K, V171A, and I185Y.

5. The non-naturally occurring isolated monomeric or dimeric lanYFP fluorescent protein of any of claim 1, 3 or 4, wherein the protein comprises a polypeptide having at least 97% sequence identity to the amino acid sequence of SEQ ID NO: 1.

* * * * *

SEQUENCE LISTING

```
<160> NUMBER OF SEQ ID NOS: 6

<210> SEQ ID NO 1
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Val Ser Lys Gly Glu Glu Asp Asn Met Ala Ser Leu Pro Ala Thr
1               5                   10                  15

His Glu Leu His Ile Phe Gly Ser Ile Asn Gly Val Asp Phe Asp Met
            20                  25                  30

Val Gly Gln Gly Thr Gly Asn Pro Asn Asp Gly Tyr Glu Glu Leu Asn
        35                  40                  45

Leu Lys Ser Thr Lys Gly Asp Leu Gln Phe Ser Pro Trp Ile Leu Val
    50                  55                  60

Pro His Ile Gly Tyr Gly Phe His Gln Tyr Leu Pro Tyr Pro Asp Gly
65                  70                  75                  80

Met Ser Pro Phe Gln Ala Ala Met Val Asp Gly Ser Gly Tyr Gln Val
                85                  90                  95

His Arg Thr Met Gln Phe Glu Asp Gly Ala Ser Leu Thr Val Asn Tyr
            100                 105                 110

Arg Tyr Thr Tyr Glu Gly Ser His Ile Lys Gly Glu Ala Gln Val Lys
        115                 120                 125

Gly Thr Gly Phe Pro Ala Asp Gly Pro Val Met Thr Asn Ser Leu Thr
    130                 135                 140

Ala Ala Asp Trp Cys Arg Ser Lys Lys Thr Tyr Pro Asn Asp Lys Thr
145                 150                 155                 160

Ile Ile Ser Thr Phe Lys Trp Ser Tyr Thr Thr Gly Asn Gly Lys Arg
                165                 170                 175

Tyr Arg Ser Thr Ala Arg Thr Thr Tyr Thr Phe Ala Lys Pro Met Ala
            180                 185                 190

Ala Asn Tyr Leu Lys Asn Gln Pro Met Tyr Val Phe Arg Lys Thr Glu
        195                 200                 205

Leu Lys His Ser Lys Thr Glu Leu Asn Phe Lys Glu Trp Gln Lys Ala
    210                 215                 220

Phe Thr Asp Val Met Gly Met Asp Glu Leu Tyr Lys
225                 230                 235

<210> SEQ ID NO 2
```

```
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atggtgagca agggcgagga ggataacatg gcctctctcc cagcgacaca tgagttacac      60
atctttggct ccatcaacgg tgtggacttt gacatggtgg tcagggcac cggcaatcca     120 aatgatggtt atgaggagtt aaacctgaag tccaccaagg gtgacctcca gttctccccc     180
tggattctgg tccctcatat cgggtatggc ttccatcagt acctgcccta ccctgacggg     240
atgtcgcctt ccaggccgc catggtagat ggctccggat accaagtcca tcgcacaatg     300
cagtttgaag atggtgcctc ccttactgtt aactaccgct acacctacga gggaagccac     360
atcaaaggag aggcccaggt gaaggggact ggtttccctg ctgacggtcc tgtgatgacc     420
aactcgctga ccgctgcgga ctggtgcagg tcgaagaaga cttaccccaa cgacaaaacc     480
atcatcagta cctttaagtg gagttacacc actggaaatg gcaagcgcta ccggagcact     540
gcgcggacca cctacacctt tgccaagcca atggcggcta actatctgaa gaaccagccg     600
atgtacgtgt tccgtaagac ggagctcaag cactccaaga ccgagctcaa cttcaaggag     660
tggcaaaagg cctttaccga tgtgatgggc atggacgagc tgtacaagta a              711

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 3

His His His His His His
1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Gly Leu Arg Ser Pro Pro Val Ala Thr
1               5                   10

<210> SEQ ID NO 5
<211> LENGTH: 219
<212> TYPE: PRT
<213> ORGANISM: Branchiostoma lanceolatum

<400> SEQUENCE: 5

Met Ser Leu Pro Ala Thr His Glu Leu His Ile Phe Gly Ser Phe Asn
1               5                   10                  15

Gly Val Asp Phe Asp Met Val Gly Arg Gly Thr Gly Asn Pro Asn Asp
            20                  25                  30

Gly Tyr Glu Glu Leu Asn Leu Lys Ser Thr Lys Gly Ala Leu Gln Phe
        35                  40                  45

Ser Pro Trp Ile Leu Val Pro Gln Ile Gly Tyr Gly Phe His Gln Tyr
```

```
                50                  55                  60
Leu Pro Phe Pro Asp Gly Met Ser Pro Phe Gln Ala Ala Met Lys Asp
 65                  70                  75                  80

Gly Ser Gly Tyr Gln Val His Arg Thr Met Gln Phe Glu Asp Gly Ala
                 85                  90                  95

Ser Leu Thr Ser Asn Tyr Arg Tyr Thr Tyr Glu Gly Ser His Ile Lys
                100                 105                 110

Gly Glu Phe Gln Val Ile Gly Thr Gly Phe Pro Ala Asp Gly Pro Val
            115                 120                 125

Met Thr Asn Ser Leu Thr Ala Ala Asp Trp Cys Val Thr Lys Met Leu
        130                 135                 140

Tyr Pro Asn Asp Lys Thr Ile Ile Ser Thr Phe Asp Trp Thr Tyr Thr
145                 150                 155                 160

Thr Gly Ser Gly Lys Arg Tyr Gln Ser Thr Val Arg Thr Asn Tyr Thr
                165                 170                 175

Phe Ala Lys Pro Met Ala Ala Asn Ile Leu Lys Asn Gln Pro Met Phe
            180                 185                 190

Val Phe Arg Lys Thr Glu Leu Lys His Ser Lys Thr Glu Leu Asn Phe
            195                 200                 205

Lys Glu Trp Gln Lys Ala Phe Thr Asp Val Met
        210                 215
```

<210> SEQ ID NO 6
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Met Val Ser Lys Gly Glu Glu Asp Asn Met Ala Ser Leu Pro Ala Thr
 1               5                  10                  15

His Glu Leu His Ile Phe Gly Ser Phe Asn Gly Val Asp Phe Asp Met
                 20                  25                  30

Val Gly Arg Gly Thr Gly Asn Pro Asn Asp Gly Tyr Glu Glu Leu Asn
             35                  40                  45

Leu Lys Ser Thr Lys Gly Asp Leu Gln Phe Ser Pro Trp Ile Leu Val
         50                  55                  60

Pro Gln Ile Gly Tyr Gly Phe His Gln Tyr Leu Pro Phe Pro Asp Gly
 65                  70                  75                  80

Met Ser Pro Phe Gln Ala Ala Met Lys Asp Gly Ser Gly Tyr Gln Val
                 85                  90                  95

His Arg Thr Met Gln Phe Glu Asp Gly Ala Ser Leu Thr Ser Asn Tyr
                100                 105                 110

Arg Tyr Thr Tyr Glu Gly Ser His Ile Lys Gly Glu Phe Gln Val Lys
            115                 120                 125

Gly Thr Gly Phe Pro Ala Asp Gly Pro Val Met Thr Asn Ser Leu Thr
        130                 135                 140

Ala Ala Asp Trp Cys Val Thr Lys Met Leu Tyr Pro Asn Asp Lys Thr
145                 150                 155                 160

Ile Ile Ser Thr Phe Asp Trp Thr Tyr Thr Thr Gly Asn Gly Lys Arg
                165                 170                 175

Tyr Gln Ser Thr Ala Arg Thr Thr Tyr Thr Phe Ala Lys Pro Met Ala
            180                 185                 190
```

| | | | | | | | | | | | | |
|---|---|---|---|---|---|---|---|---|---|---|---|---|
|Ala|Asn|Ile|Leu|Lys|Asn|Gln|Pro|Met|Phe|Val|Phe|Arg|Lys|Thr|Glu|
| | |195| | | |200| | | |205| | | | | |
|Leu|Lys|His|Ser|Lys|Thr|Glu|Leu|Asn|Phe|Lys|Glu|Trp|Gln|Lys|Ala|
| |210| | | |215| | | |220| | | | | | |
|Phe|Thr|Asp|Val|Met|Gly|Met|Asp|Glu|Leu|Tyr|Lys| | | | |
|225| | | |230| | | |235| | | | | | | |